United States Patent [19]
Dreyer et al.

[11] Patent Number: 6,094,301
[45] Date of Patent: Jul. 25, 2000

[54] FOLDING RACK FOR VERTICAL PRESENTATION OF MICROSCOPE SLIDES

[75] Inventors: Dale A. Dreyer, Vadnais Heights; Benjamin L. Behler, Maplewood, both of Minn.

[73] Assignee: Systec Inc., New Brighton, Minn.

[21] Appl. No.: 09/338,305

[22] Filed: Jun. 22, 1999

Related U.S. Application Data

[63] Continuation-in-part of application No. 09/079,794, May 15, 1998, Pat. No. 6,020,995.

[51] Int. Cl.[7] .............................. G02B 21/26; G02B 21/34
[52] U.S. Cl. ........................... 359/396; 359/391; 359/398
[58] Field of Search ..................... 359/391–398, 359/368; 356/244; 206/454–456; 422/100–104

[56] References Cited

U.S. PATENT DOCUMENTS

| | | |
|---|---|---|
| 595,516 | 12/1897 | Baird . |
| 902,153 | 10/1908 | Logan . |
| 1,035,552 | 8/1912 | Doering . |
| 1,274,306 | 7/1918 | Moisson . |
| 2,961,101 | 11/1960 | Hutton . |
| 3,235,096 | 2/1966 | Hallock et al. . |
| 3,713,771 | 1/1973 | Taylor et al. . |
| 4,641,930 | 2/1987 | Podvin et al. ........................ 359/391 |
| 4,765,469 | 8/1988 | Seifert .................................. 206/309 |
| 4,801,431 | 1/1989 | Cuomo et al. ....................... 422/104 |
| 5,002,736 | 3/1991 | Babbitt et al. ....................... 422/100 |
| 5,149,244 | 9/1992 | Webber et al. ...................... 414/417 |
| 5,350,069 | 9/1994 | Agwu .................................. 206/454 |
| 5,762,201 | 6/1998 | Whalen ............................... 206/711 |

*Primary Examiner*—Thong Nguyen
*Attorney, Agent, or Firm*—Haugen Law Firm PLLP

[57] ABSTRACT

A microscope slide receptacle system for positionably receiving and releasably holding specimen retaining microscope slides in a generally vertical disposition. The system includes a plurality of hinged first and second frames each frame comprising a generally inverted "U"-shaped changer and having complementary coupling hinges for intercoupling multiple frames together to form the system. A releasable clip is fastened to the frame structure for engaging and supporting the slides. Each frame has a support hanger along the upper surface to permit coupling to a system support.

4 Claims, 7 Drawing Sheets

FOLDING RACK FOR VERTICAL PRESENTATION OF MICROSCOPE SLIDES

CROSS-REFERENCE TO RELATED APPLICATION

The present application is a continuation-in-part of our application Ser. No. 09/079,794, filed May 15, 1998 now U.S. Pat. No. 6,020,995, entitled "FOLDING RACK FOR MICROSCOPE SLIDES" now U.S. Pat. No. 6,020,995, and assigned to the same assignee as the present application.

BACKGROUND OF THE INVENTION

The present invention relates to an improved receptacle or holder for vertical presentation of microscope slides such as those utilized for specimen retention in scientific, medical or medically related procedures. The slide receptacles of the present invention are designed to positionably receive and hold specimen retaining microscope slides in a foldable array designed for minimizing slide-to-holder contact areas while allowing for appropriate drainage of aqueous and other solutions therefrom. The holders of the present invention include a linkage system to permit simultaneous articulation of a plurality of slides, so as to present the slides or groups of slides in either a flat planar array or in appropriate closely spaced vertical orientation. Stated briefly, the slide receptacles of the present invention positionably receive the slides in an appropriate array, while at the same time the surface of contact between the slides and the support is reduced. The configuration facilitates convenient release and manual grasping or gripping of the slides along the edge surfaces when desired.

In the past, receptacles have been provided for retaining microscope slides in predetermined or proper orientation for exposure of the slides to various operations or procedures, with the orientation depending upon the immediate application. Typical operations or procedures include exposure to washing and/or rinsing solutions, as well as exposure to various controlled environments, such as one of controlled temperature and humidity. In order to enhance and otherwise facilitate appropriate handling of the slides, the present invention provides for minimal areas or zones of contact between the slides and the holder, and further provides and facilitates manual grasping and/or gripping of the individual slides for removal and/or transfer from the holder. The configuration of the holders of the present invention are such that the area of contact with the slide is minimized to facilitate rapid and efficient liquid drainage, such as aqueous or other solutions which typically are in contact with the slides, as well as to facilitate manual manipulation of the slides.

SUMMARY OF THE INVENTION

In accordance with the present invention, a microscope slide receptacle means is provided for positionably receiving and holding specimen retaining slides, with the receptacle means comprising a frame which defines a holder for enhanced support and handling of the slides being retained. The holder is of a generally inverted "U"-shaped configuration with a laterally extending upper base support and a pair of legs extending downwardly from opposed ends of the base. The base support has a generally flat clip receiving pad filling the zone which is created between the base and legs so as to position the top edge of the slide immediately below the surface of the base. In this fashion, the area or zone of contact between the holder and the slide is minimal, thereby reducing the risk of cross-contamination between the slide and its support.

In addition, the frame means of the present invention is designed to provide a receptacle for retaining or holding the slides in registration, one with another. Appropriate registration is achieved by means of utilizing the clips which are coupled to the downwardly extending legs. The clips reduce the area of contact between the surface of the slide and other surfaces. These designs allow more rapid and complete drainage of liquids from the slide, while at the same time holding the slides in accurate registration, as well as in a configuration which facilitates simple manual slide removal.

An additional feature of the present invention is the utilization of hinge means between mutually adjacent frame pair components. Specifically, complementary hinge means are coupled from points laterally outwardly of each of the frame components for simultaneous articulating rotational motion of a plurality of cradles. This linkage means is designed to provide accordion-like folding.

Therefore, it is an object of the present invention to provide an improved microscope slide receptacle means which comprises a frame defining a support frame assembly, with the assembly being designed to facilitate rapid drainage of liquid from the slides, and further being designed to minimize the areas of contact between the slides and the holder.

It is a further object of the present invention to provide an improved slide receptacle means which utilizes holders articulated for simultaneous rotational motion, with the articulation maintaining the individual slides comprising an array of slides in appropriate and desired vertical orientation and in a desired registration.

It is yet a further object of the present invention to provide an improved receptacle system for microscope slides which facilitates removal of the slides manually.

Other and further objects and features of the present invention will become apparent to those skilled in the art upon a study of the following specification, appended claims, and accompanying drawings.

DESCRIPTION OF THE PREFERRED EMBODIMENT

Figures 1, 2:
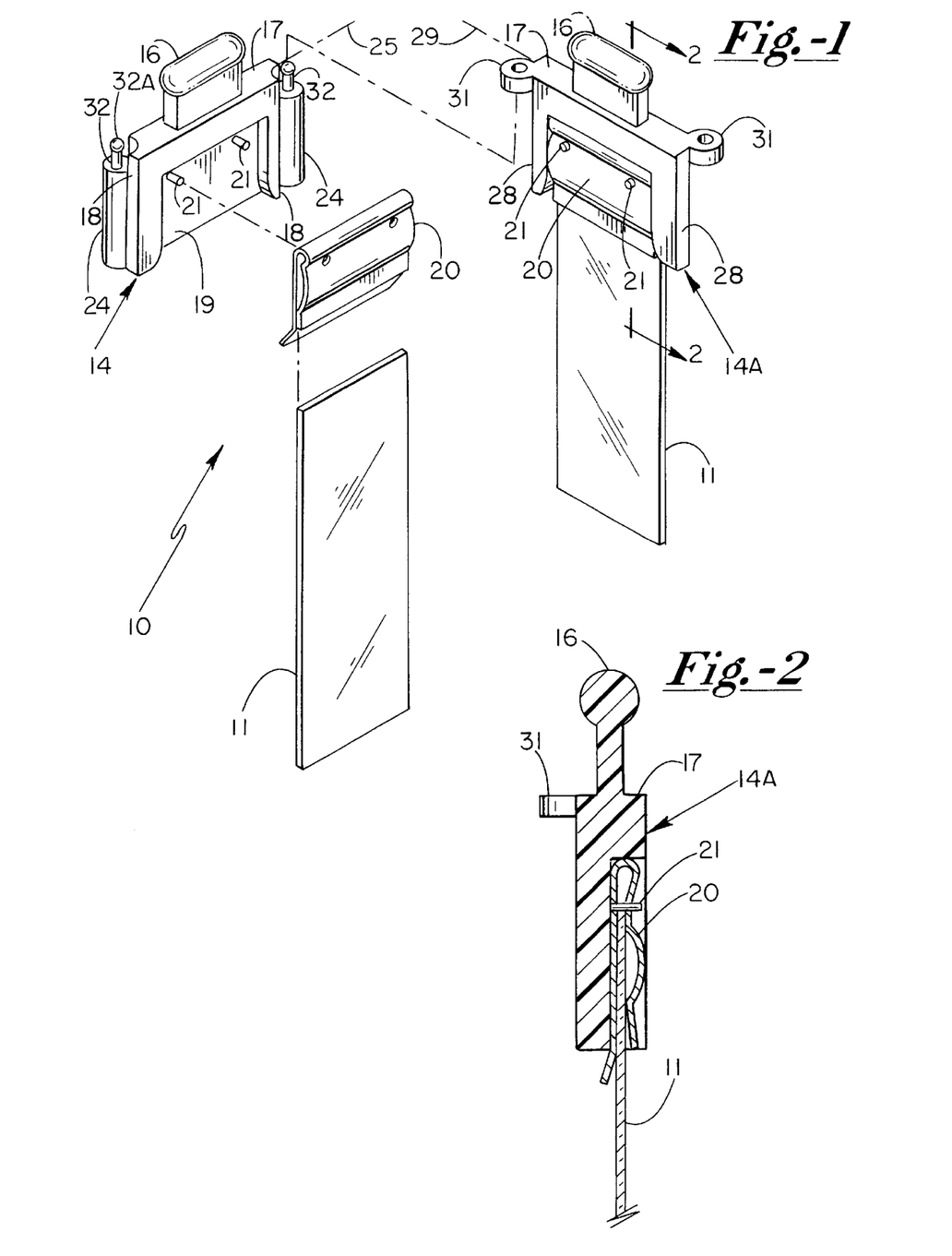
FIG. 1 is a perspective view, partially exploded, of a pair of frame components arranged in side-by-side relationship, and with a microscope slide being shown with one of the frame components, and with an appropriate linkage means being illustrated for coupling the two frame components together, one to the other.
FIG. 2 is a side elevational view taken along the line and in the direction of the arrows 2—2 of FIG. 1.

With attention being directed to FIG. 1 of the drawings, the array of two microscope slide receptacle means generally designated 10 is provided for positionably receiving and holding specimen retaining microscope slides such as slide 11 therewithin. The receptacle means comprises first and second frame means generally designated 14 and 14A, each defining a holder for supporting the slides. Each frame means comprises an inverted "U"-shaped hanger 16 with a generally laterally extending horizontally disposed base 17 with a pair of legs 18—18 extending downwardly in depending relationship from opposed ends of the base 17. The inverted "U"-shaped hanger defines a zone in which a clip mounting pad 19 is positioned. A slide retaining clip 20 is secured to pad 19 by any convenient means, such as on receiving pegs 21—21. The clip is preferably a spring biased clip designed to releasably hold a slide therein while in vertical disposition. As indicated, the slide is held immediately beneath the surface of base 17 with the cross-sectional thickness of the frame means being greater than that of the microscope slide to be retained therein.

Hinge means are provided for coupling first and second complementary frames 14 and 14A together, with the hinge means comprising first and second complementary coupler halves. Hinge means are preferably integrally attached to the right and left side edge surfaces of each of the frame means. The arrangement is such that the right edge surface of each of the first frame components, such as frame component 14 has a first coupler half 24 positioned forwardly of the longitudinal axis 25 of the frame means 14, for example. The left edge surface of frame component 14 has a first coupler half integrally attached thereto and positioned rearwardly of the longitudinal axis 25. In order to form the second complementary frame component, the left edge surface 28 of said second frame means 14A has a second coupler half 31 positioned forwardly of the longitudinal axis 29, and with the right edge surface 28 having a second complementary coupler half 31 positioned rearwardly of longitudinal axis 29. In this situation, the arrangement is such that accordion-like folding of the frame means is accommodated.

Figure 3:
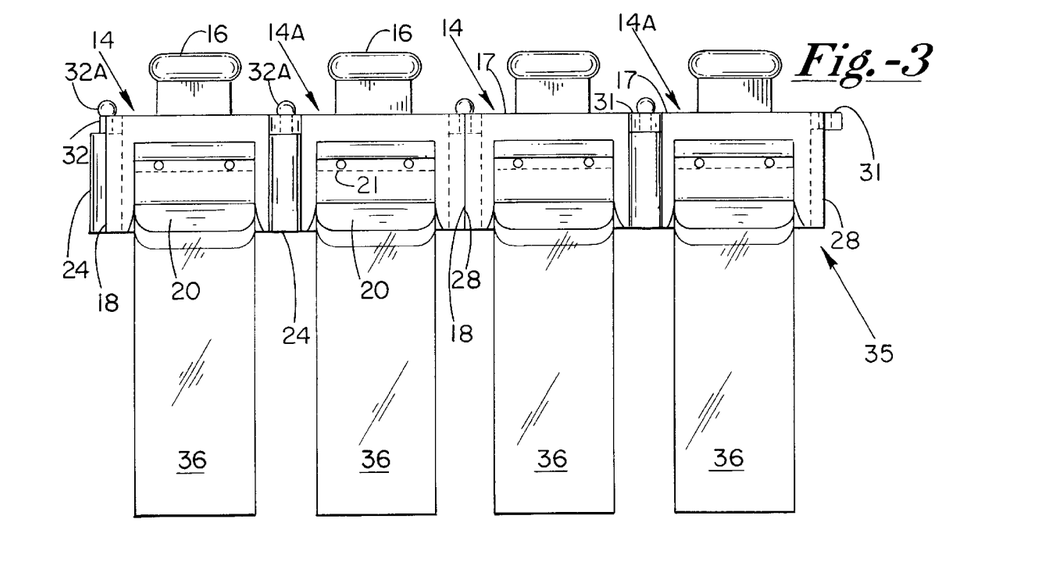
FIG. 3 is a front elevational view of an array of frame components coupled together, and shown in expanded disposition.

With attention now being directed to FIGS. 3–6 inclusive, the array of frames generally designated 35 illustrated in FIG. 3 consists of two pair of frame means such as shown and described at 14 and 14A (FIG. 1), with the array being shown in fully opened disposition. A plurality of microscope slides such as at 36—36 are shown in vertical presentation.

Figure 4:
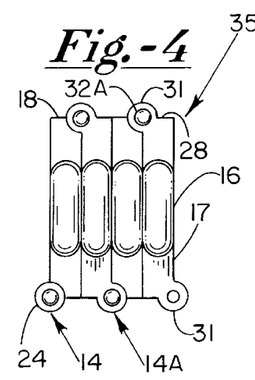
FIG. 4 is a top plan view of the frame components illustrated in FIG. 3, with the frame components or members being shown in closed configuration.
Figure 5:
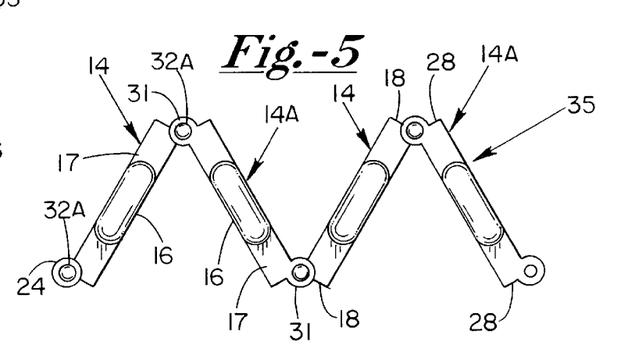
FIG. 5 is a top plan view similar to FIG. 4, and illustrating the frame members in partially open configuration.
Figure 6:
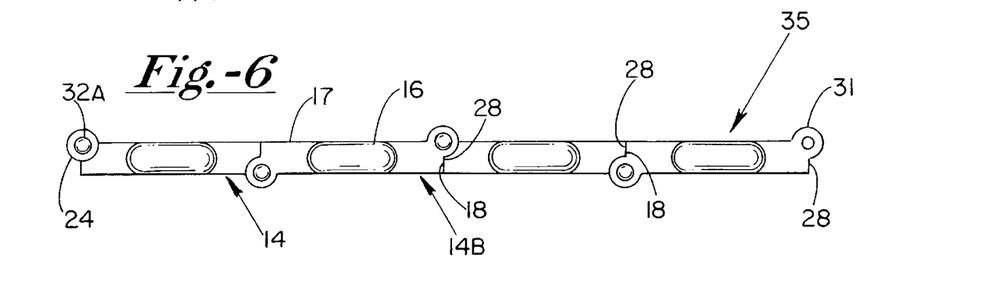
FIG. 6 is a top plan view of the array illustrated in FIG. 3.

As indicated hereinabove, the arrays may be folded in accordion-like fashion, and the arrangement of FIG. 3 is shown in closed disposition in FIG. 4. A partially opened configuration is illustrated in FIG. 5, with FIG. 6 being the top plan view of the array as illustrated in FIG. 3.

In order to appropriately articulate and support the individual frame components, hanger tabs as at 16 are utilized. These hanger tabs may be inserted within appropriate hanging slots, as required for the individual application.

With attention again being directed to FIG. 1, it will be noted that the coupling arrangement includes two posts or pins such as at 32—32 are provided, with the pins being received within bores formed in pad 19, and thereby accommodating relative pivotal motion between the individual frame components. An expanded bead or head as at 32A is arranged at the upper distal end of posts 32—32.

Figure 7:
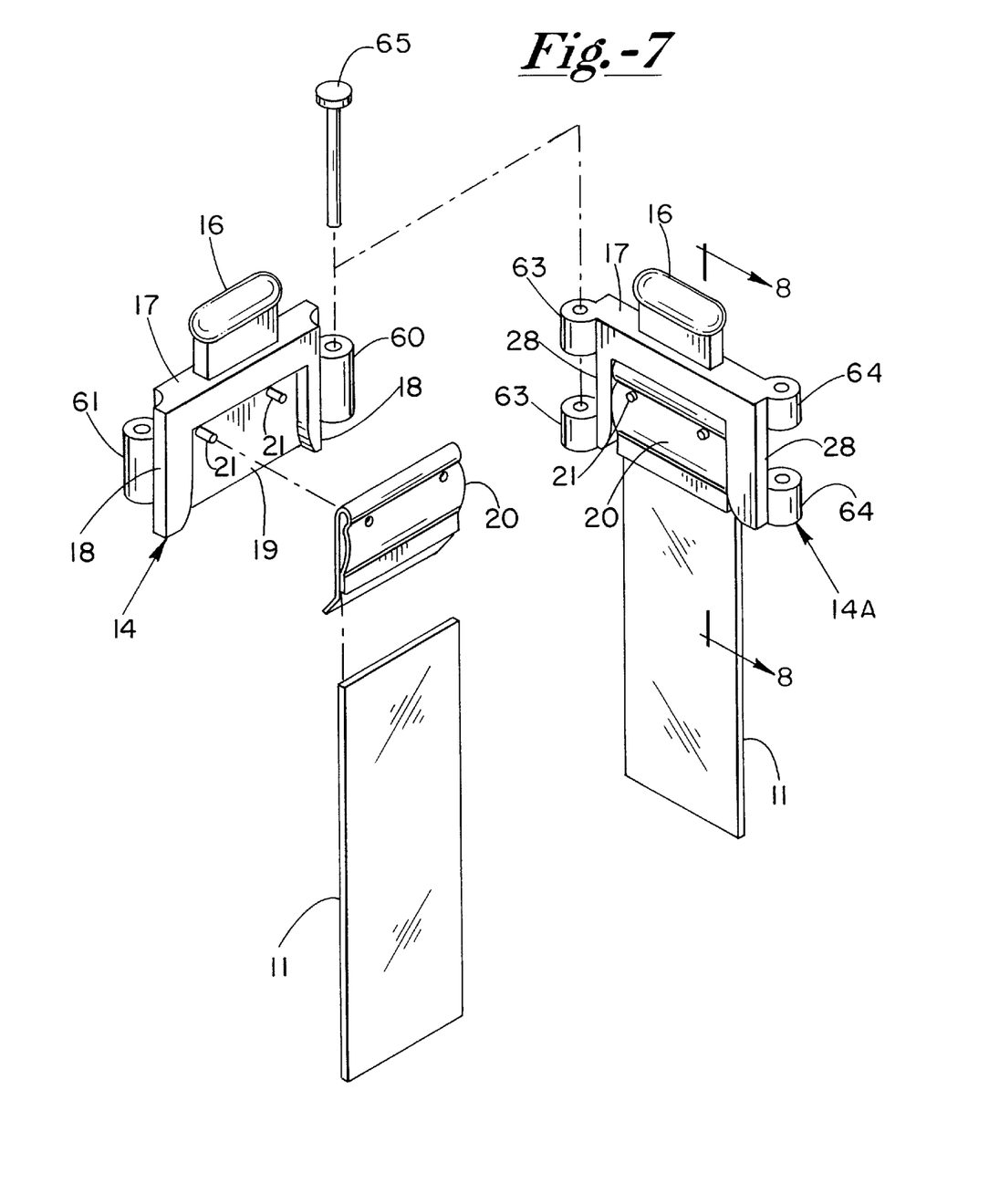
FIG. 7 is a partially exploded view of a modified form of frame components arranged in side-by-side relationship, and with a microscope slide being shown with one of the frame components, and with an appropriate linkage means being illustrated for coupling the two frame components together one to the other.
Figure 8:
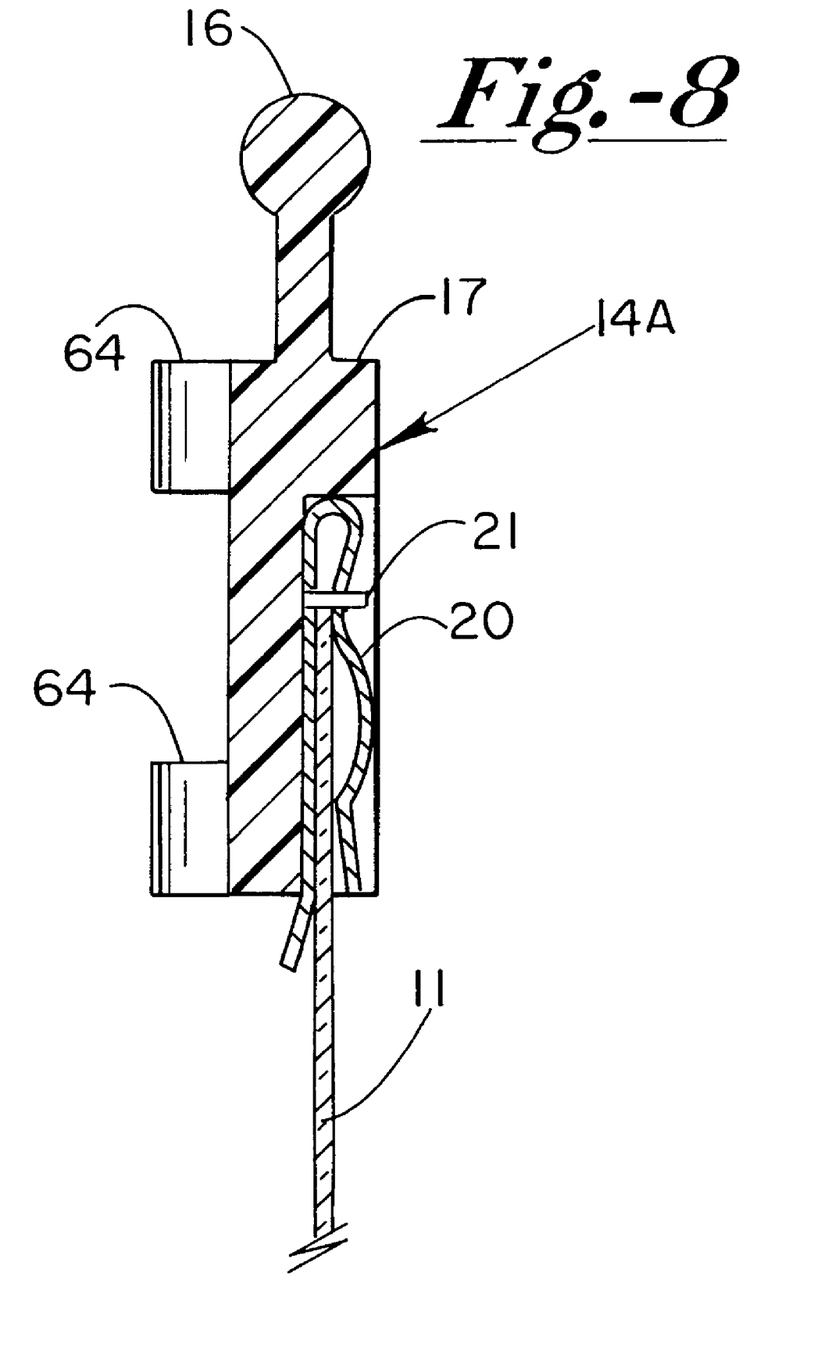
FIG. 8 is a side elevational view taken along the line and in the direction of the arrows 8—8 of FIG. 7.
Figure 9:
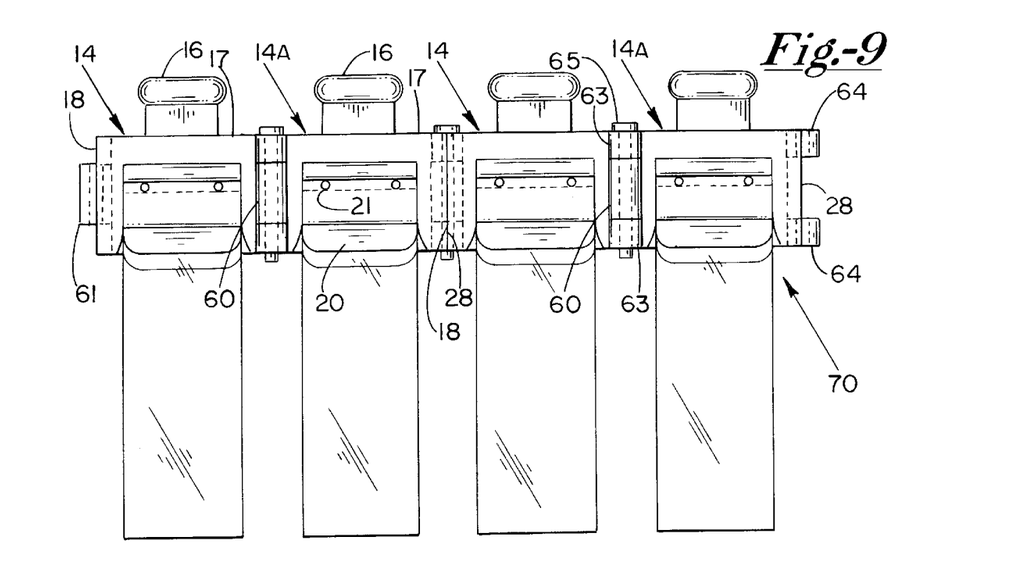
FIG. 9 is a front elevational view of an array of the frame components coupled together as illustrated in the embodiment of FIG. 7, and shown in expanded disposition.
Figure 10:
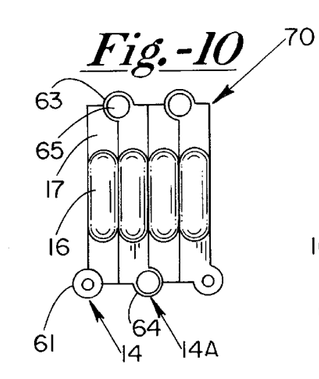
FIG. 10 is a top plan view of the frame components illustrated in FIG. 9, with the frame components or members being shown in closed configuration.
Figure 11:
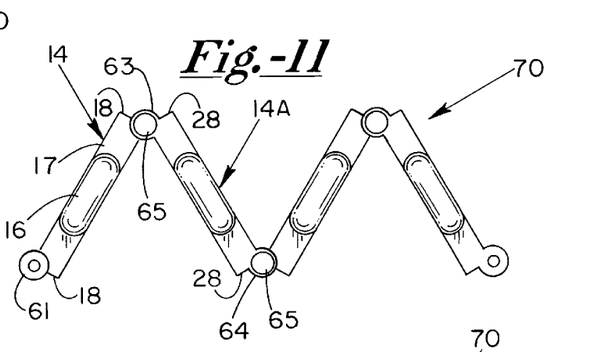
FIG. 11 is a top plan view similar to FIG. 10, and illustrating the frame members in partially open configuration.
Figure 12:
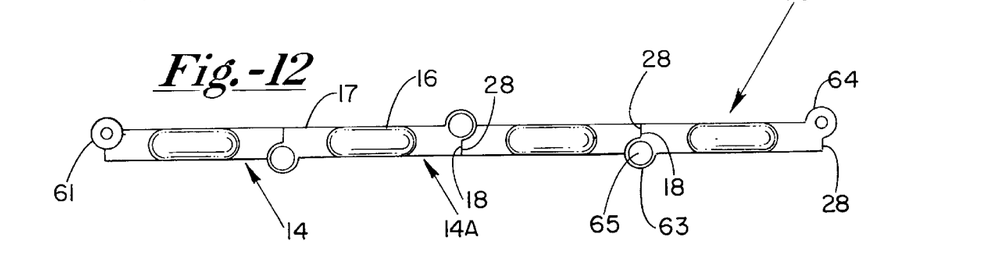
FIG. 12 is a top plan view of the array illustrated in FIG. 9.

With attention now being directed to FIG. 7 of the drawings, an alternate form of coupler half pairs is utilized for coupling individual frame components together. The configuration of the frame means as illustrated in FIG. 7 is the same as that illustrated in FIGS. 1–6, with the exception of the design of the individual coupler halves. In the embodiment of FIGS. 7–12, a first coupler half in the form of a central sleeve as at 60 and 61, together with a complementary second coupler half in the form of spaced apart sleeves 63—63 and 64—64. Hinge pin 65 is received within the bore of the sleeves when in aligned disposition, such as in the configuration illustrated in FIGS. 9–12 inclusive. The views of FIGS. 7–12 disclose the configuration of the individual frame components being coupled together in an array such as array generally at 70 (FIG. 9), with the array 70 being substantially the same as that array of FIG. 3, with the exception of the individual coupler elements.

Figure 13:
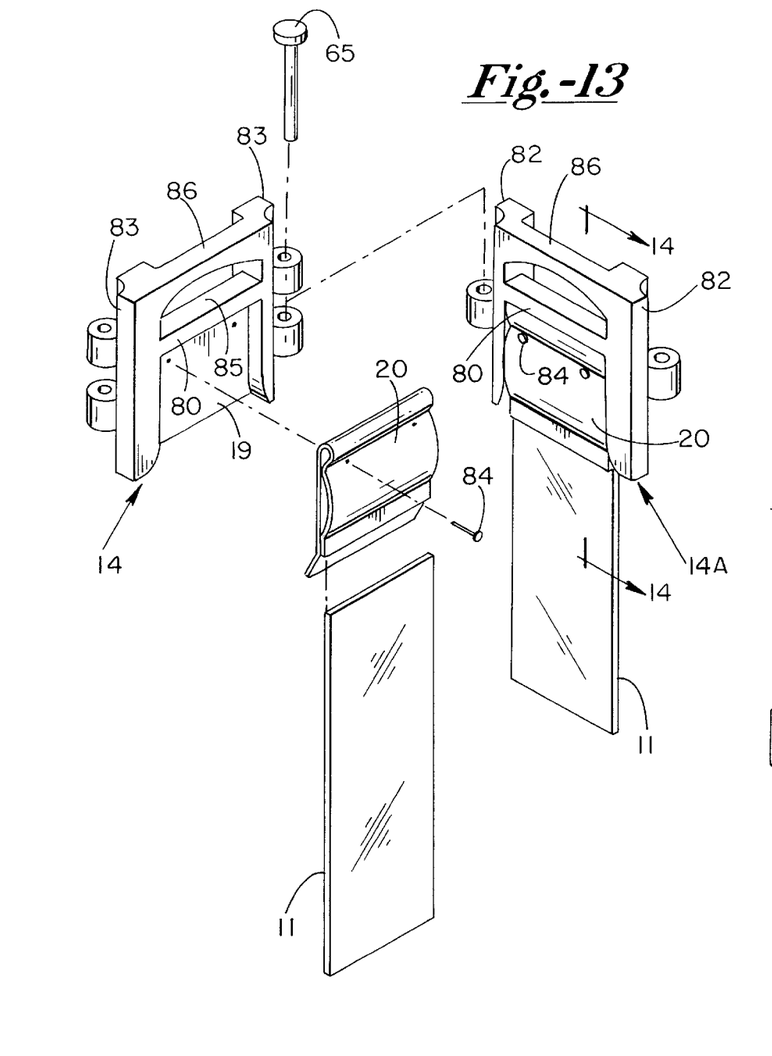
FIG. 13 is a perspective view of a second alternative embodiment, partially exploded, of a pair of frame components arranged in side-by-side relationship, and with a microscope slide being shown with one of the frame components, and with an appropriate linkage means being illustrated for coupling the two frame components together, one to the other.
Figure 14:
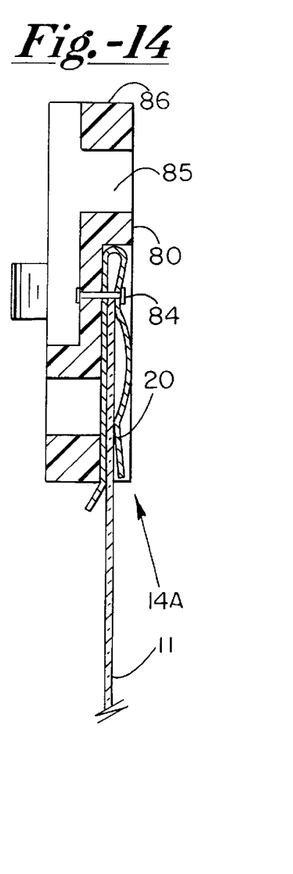
FIG. 14 is a side elevational view taken along the line and in the direction of the arrows 14—14 of FIG. 13.

With attention now being directed to FIGS. 13–18 of the drawings, the frame means is slightly modified from that illustrated in FIGS. 1–12 inclusive. In this arrangement, the base 80 is positioned medially along vertical legs 82—82 in frame means 14A and 83—83 in frame means 14, and an upper cross-member 86 is provided to form a medial finger-engaging or gripping opening is provided as at 85. The coupler halves are similar to those illustrated in FIGS. 7–12, with the exception of the matching axial length. Also, as is indicated in FIG. 13, the clip holder 20 is secured to pad 19 by means of rivets 84—84.

Figure 15:
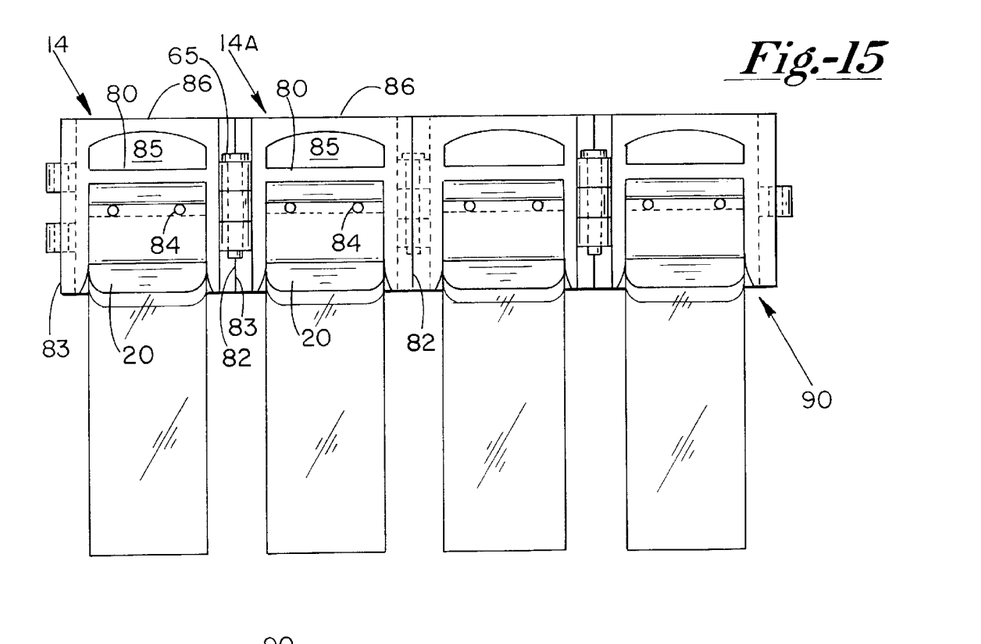
FIG. 15 is a front elevational view of an array of frame components coupled together, and shown in expanded disposition.
Figures 16, 17, 18:
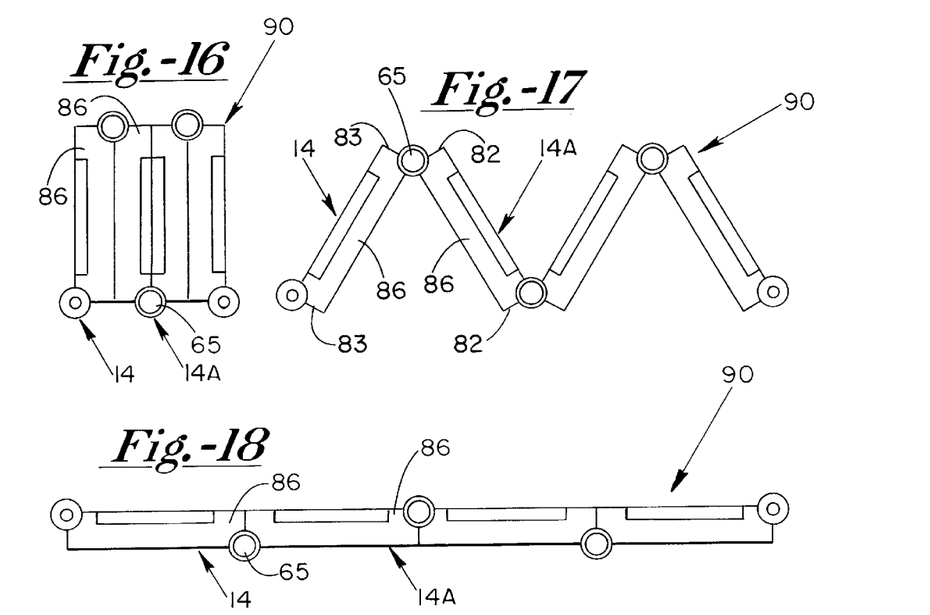
FIG. 16 is a top plan view of the frame components illustrated in FIG. 14, with the frame components or members being shown in closed configuration.
FIG. 17 is a top plan view similar to FIG. 16, and illustrating the frame members in partially open configuration.
FIG. 18 is a top plan view of the array illustrated in FIG. 15.

The array of frame means generally designated 90 illustrated in FIG. 15 is essentially the same as that of the arrays 35 and 70 hereinabove, as are the individual configurations of FIGS. 16–18 inclusive.

It will be noted that the cross-sectional thickness of each of the frame components is such that the individual microscope slides, while being held within the assembly or array will not be in mutual contact, one with the other.

It will be appreciated that various modifications may be made in the embodiments as illustrated herein without actually departing from the spirit and scope of the present invention.

What is claimed is:

1. Microscope slide receptacle means for positionably receiving and releasably holding specimen retaining microscope slides and comprising a plurality of hinged first and second frame means each with right and left surfaces and each with complementary coupling means, each with a longitudinal axis and each being arranged for fastening a releasable slide retaining means for engaging and supporting said slides, said frame means being characterized in that:

(a) said frame means comprising a generally inverted "U"-shaped hanger with a generally horizontally disposed base having an upper surface with a support hanger therealong, and with laterally disposed vertical legs depending from opposed ends thereof;

(b) said horizontally disposed base having a slide retainer mounting pad with said slide retaining means associated therewith and disposed beneath said base between each of said legs, with said slide retaining means being positionably mounted beneath said base, thereby enabling a slide to be releasably held by said slide retaining means in vertical disposition immediately beneath said base and between said legs;

(c) each of said first and second frame means having hinge means comprising first and second complementary coupler halves inwardly attached to opposed right and left side edge surfaces respectively of said frame means, (1) with the said right edge surface of each first frame means having a first coupler half positioned forwardly of said longitudinal axis, and with the said left edge surface having a first coupling half positioned rearwardly of said longitudinal axis; and (2) with said left edge surface of each second frame means having a second coupler half positioned forwardly of said longitudinal axis and with said right edge surface having a second coupler half positioned rearwardly of said longitudinal axis;

(d) the arrangement of said coupler halves being such that accordion folding of said frame means and microscope slides retained therein is accommodated.

2. The frame means as defined in claim 1 being particularly characterized in that said slide retaining means is a spring clip.

3. The frame means as defined in claim 1 being particularly characterized in that the cross-sectional thickness of each of said frame means is greater than the cross-sectional thickness of the microscope slide to be retained therein.

4. The frame means as defined in claim 1 wherein said slide retaining means is a spring-biased clip secured to said slide retainer mounting pad.

* * * * *